United States Patent [19]

Morales-Quintero

[11] Patent Number: 5,297,852
[45] Date of Patent: Mar. 29, 1994

[54] SECURITY HARNESS FOR ENFEEBLED ADULT PATIENTS

[75] Inventor: Carmen D. Morales-Quintero, Carolina, P.R.

[73] Assignee: Commonwealth of Puerto Rico, San Juan, P.R.

[21] Appl. No.: 12,378

[22] Filed: Feb. 2, 1993

[51] Int. Cl.⁵ .............................................. B60R 22/12
[52] U.S. Cl. .................................... 297/467; 297/485; 128/846
[58] Field of Search .................. 297/464, 467, 485; 128/846, 869

[56] References Cited

U.S. PATENT DOCUMENTS

| | | | |
|---|---|---|---|
| 1,376,625 | 5/1921 | Johnston . | |
| 2,486,114 | 10/1949 | Cataldo . | |
| 2,851,033 | 9/1958 | Posey | 297/484 X |
| 4,050,737 | 9/1977 | Jordan . | |
| 4,170,991 | 10/1979 | Kella | 297/467 |
| 4,467,945 | 8/1984 | Schaapveld | 297/467 X |
| 4,509,797 | 4/1985 | Mullaly | 297/467 X |
| 4,657,005 | 4/1987 | Williamson . | |
| 4,860,771 | 8/1989 | Burgos . | |
| 4,927,211 | 5/1990 | Bolarek | 297/467 X |
| 5,016,650 | 5/1991 | Marlar . | |
| 5,215,354 | 6/1993 | Grene | 297/485 |

*Primary Examiner*—Peter R. Brown
*Attorney, Agent, or Firm*—Oblon, Spivak, McClelland, Maier & Neustadt

[57] ABSTRACT

A security harness has front and rear panels joined by a crotch panel with elongated straps extending from outer corners of the front and rear panels for securing to anchoring points located behind and above at least the waist of a patient wearing the harness, and in either a seated or prone position. A waist strap is fixed to the front panel straps and extends laterally of those straps for securing to other anchoring means to either side of the patient.

2 Claims, 3 Drawing Sheets

SECURITY HARNESS FOR ENFEEBLED ADULT PATIENTS

FIELD OF THE INVENTION

This invention relates to a security harness for adult patients subject to inadvertent sliding or falling from a support for the patient and more particularly to a harness which is equally effective for a patient sitting upright in a chair or lying prone on a bed.

BACKGROUND OF THE INVENTION

A number of patents have been issued for harnesses for infants but very few for harnesses for adults. Adult patients, particularly elderly patients sometimes have only slight control over their bodily movements and, when seated in a chair, can slump over at the waist or even slide entirely off a chair possibly injuring themselves. In like manner such patients, when lying on a bed, can roll or slide off the bed with similar bad results. Thus there is a need for both a harness for a seated adult patient and a harness for an adult patient lying prone, but having separate harnesses each adapted for those entirely different positions of a patient is expensive, and even when a nursing facility is supplied with separate harnesses for prone or sitting patients, removing one type of harness for replacement by the other is difficult for the care-giver, and often traumatic for the patient. Hence there has been need for a universal harness which will serve a patient with equal facility whether he is sitting on a chair or lying down on a bed, and the broad object of the invention is to provide such a dual purpose harness especially adapted for use by adult patients.

SUMMARY OF THE INVENTION

The harness consists of front and rear panels joined together by a crotch panel. Extending outwardly from outer corners of the front and rear panels are elongated straps and attached to those straps fixed to the front panel is a waist strap spaced beyond the front panel and having elongated end parts extending at right angles away from the front panel straps. Thus when the rear, crotch and front panels have been applied to a patient and the latter seated in a wheel chair, say, the front and rear panel straps may be secured to or around anchors, such as the wheel chair handles, above and behind the patient's waist and the elongated end parts of the waist strap may be secured other anchors such as the side bars of the back of the chair to which the ends may be tied, or they may be tied together behind the chair back. When the patient is to be moved to a prone position on a bed, the straps are released from their anchors on the chair, the harness is held in place by a care-giver as the patient is helped onto the bed and thereafter the front and rear panel straps are tied to or around anchors at the head of the bed and the ends of the waist strap are tied to or around anchors at the sides of the bed.

A particular advantage of the harness of the invention, in addition to its dual use as described above, is that it permits a patient to have a wide range of movement while he is securely protected against falling from his support unit, be it a bed or a chair. The crotch panel is particularly suited to retaining diapers in place for those patients requiring diapers.

BRIEF DESCRIPTION OF THE DRAWINGS

The invention will be better understood when the following detailed description is read in conjunction with the accompanying drawings wherein.

Figure 1:
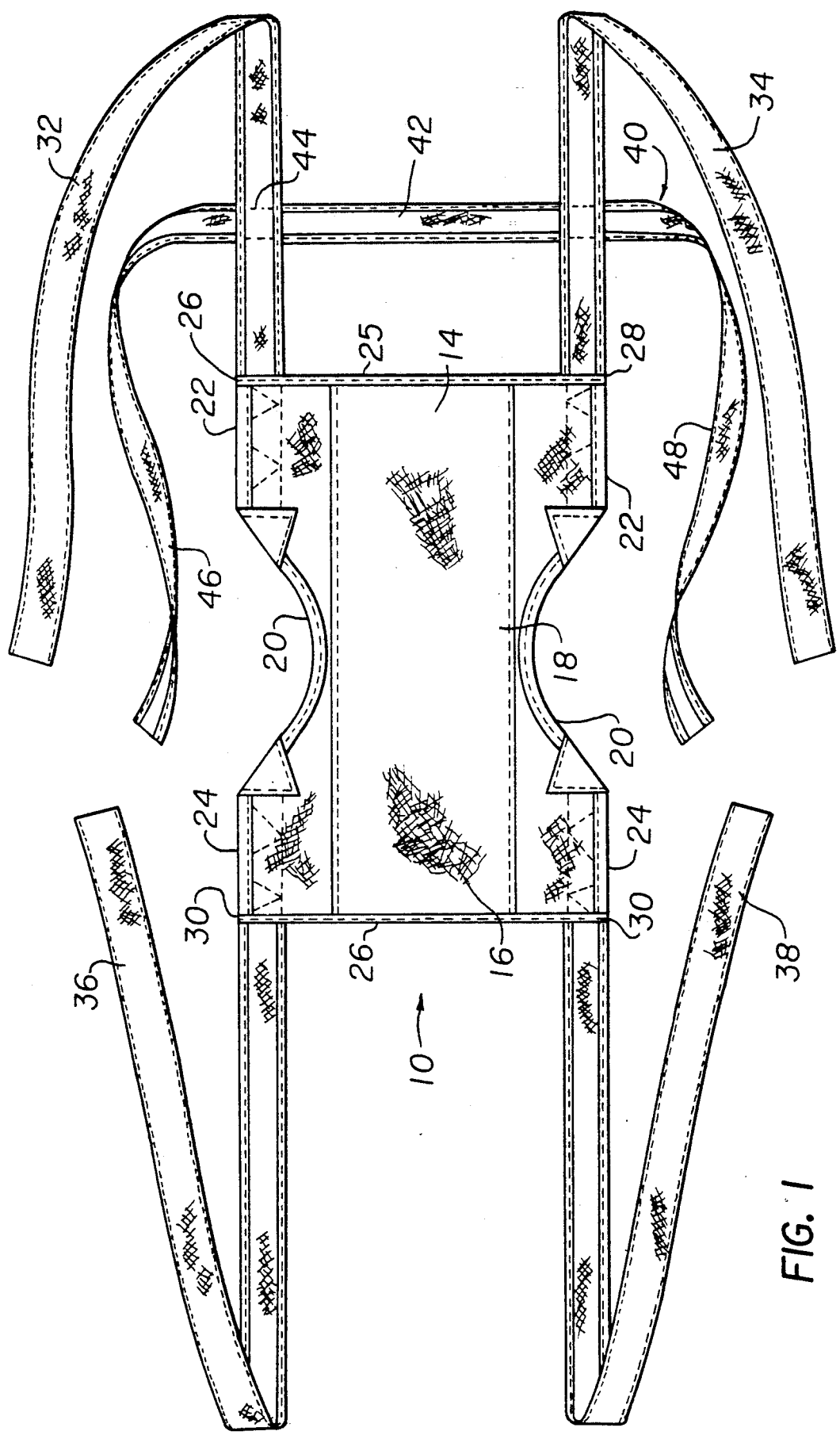
FIG. 1 is a horizontal plan view of the harness of the invention.
Figure 2:
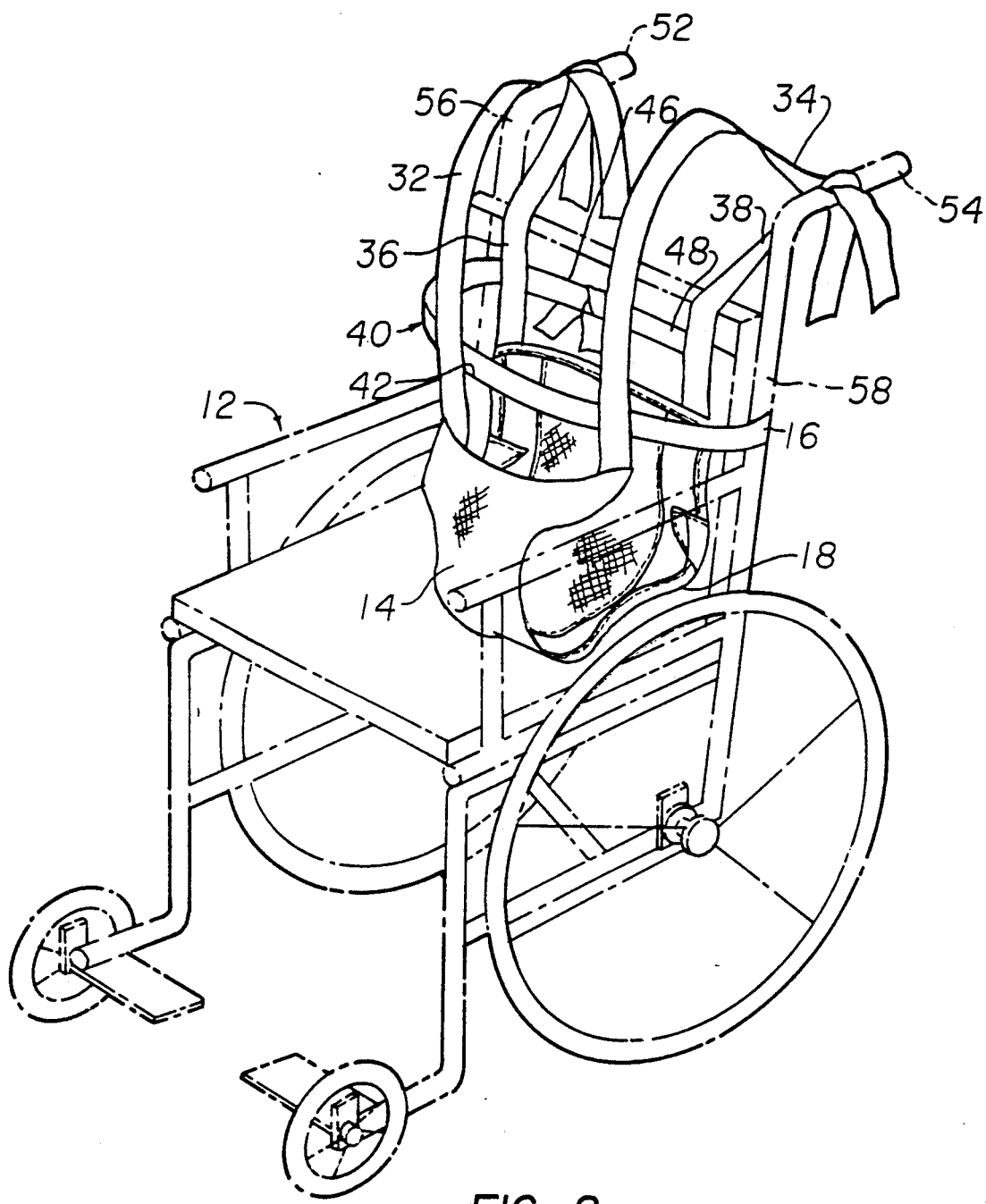
FIG. 2 is a perspective view of the harness as it would appear when applied to a patient seated on a wheel chair.

Referring now to the drawings and particularly FIG. 1, the numeral 10 broadly designates the harness of the invention which is designed for use with adult patients to prevent them from falling or sliding from a support unit for the patient, either a bed (not shown) or a chair, such as the wheel chair 12, illustrated in FIG. 2. The harness 10 comprises front and rear panels 14, 16 joined together by a crotch panel 18 having laterally spaced side edges which are inwardly recessed, as shown at 20, to accommodate the legs of a patient. The front and rear panels 14, 16 may be substantially rectangular with respective laterally spaced, parallel side edges 22, 24 and free outer end edges 25, 26, which may be normal to the side edges as shown and define, with the side edges 22, 24, pairs of laterally spaced corners 28, 30.

Elongated straps 32, 34, 36 and 38 have inner ends fixed respectively to each of the respective corners 28, 30 and extend outwardly therefrom parallel to the side edges 22, 24 of the respective front and rear panels 14, 16. A waist strap 40 has a central part 42 spaced outwardly beyond the free outer end edge 25 of the front panel and secured, as by stitching 44, at right angles to both of the front panel straps 32, 34. The waist strap 40 has elongated end parts 46, 48 extending in opposite directions away from the respective front panel straps 32, 34.

Figure 3:
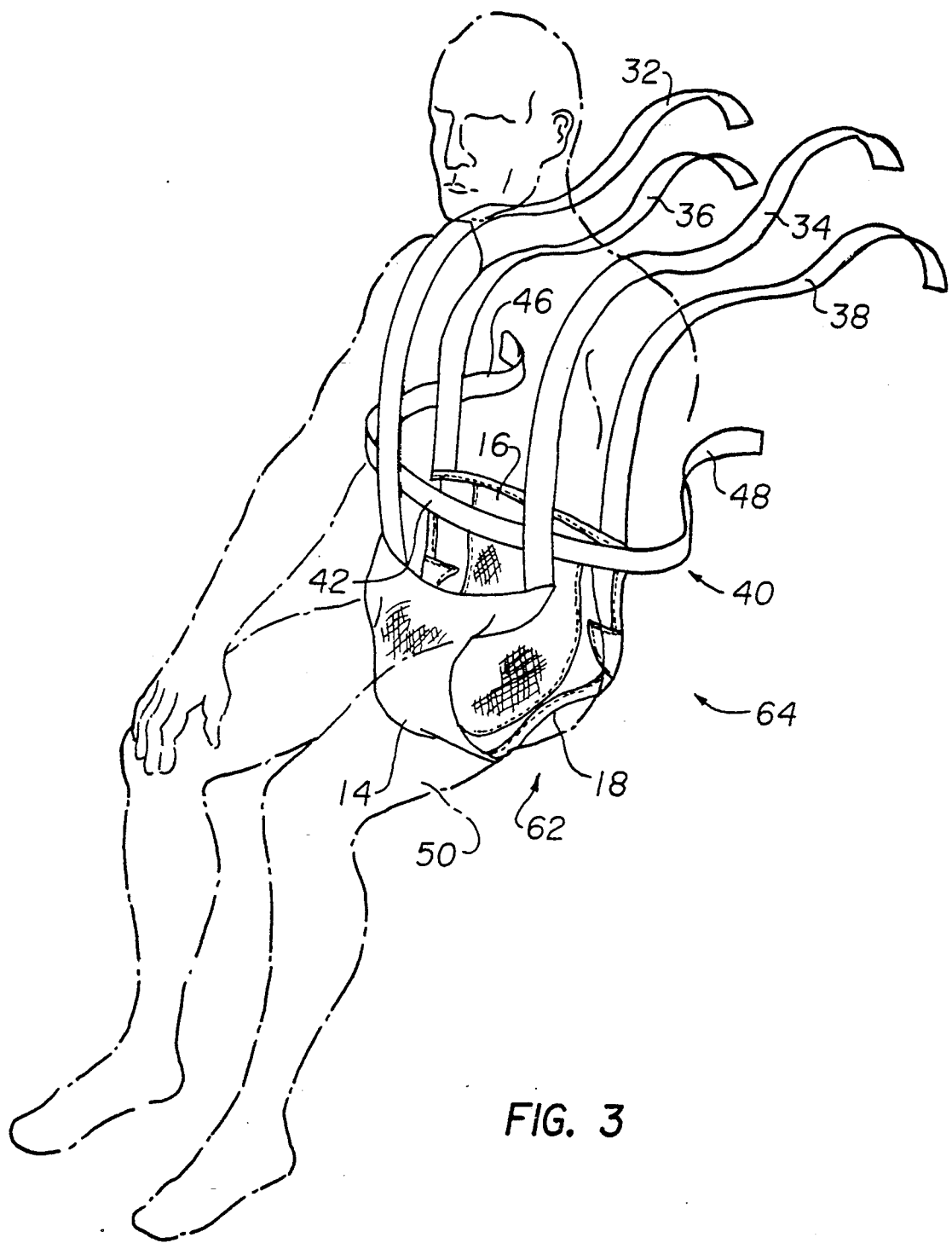
FIG. 3 is a perspective view showing the harness applied to a patient who may be in either a substantially prone position or a seated position.

The front and rear panel straps 32, 34 and 36, 38, respectively, have a length such that when the harness 10 is disposed on a patient 50, as seen in FIG. 3, lying or seated on a support unit, either a bed (not shown) or a chair, such as the previously mentioned wheel chair 12 seen in FIG. 2, the straps may be secured around anchoring points disposed behind and above at least the patient's waist. When seated in the wheel chair 12, the anchoring points for both sets of straps could conveniently be the handles 52, 54 to which the straps 32, 36 and 34, 38, could respectively be tied. The end parts 46, 48 of the waist strap 40 have lengths for connection around other anchoring points disposed to either side of a patient, such as the vertical side bars 56, 58 of the wheel chair 12 to which the end parts of the waist strap may be directly tied, if there is a clear space on the bars, or the end parts may be tied together around the side bars as shown at 60 in FIG. 2.

With reference now to FIG. 3, the previously referred to patient 50, shown in phantom lines, wearing the harness of the invention is pictured in a position which is seated when the figure is viewed in the direction of the arrow 62 or prone when the figure is viewed substantially in the direction of the arrow 64. In the seated position the straps could be secured to anchor points as described in connection with FIG. 2. When the patient is in a prone or near prone position, it should be apparent that the straps 32, 36 and 34, 38 could be brought to the end of the bed beyond the patient's head and there tied to or around anchoring points which might be bars at the head of the bed or a head board. The parts 46, 48 could be tied to the bed frame on either side of the patient.

The harness may be made throughout of soft denim or other suitable material and the crotch panel is lined for use with disposable diapers. Because the harness is intended for use with enfeebled but otherwise normal adults, it permits free movement by the patient of his arms, legs and head and a wide range of movement of the torso. As is clear in FIG. 3, normal clothes can be worn below the waist and also above the waist, with the straps having an appearance similar to conventional suspenders. In a word, the harness of the invention is a preventor and not a restrainer and is designed, when worn, to maintain the dignity of the patient to the maximum.

Having now described the invention, what is claimed is:

1. A security harness for preventing a patient from falling from a unit supporting said patient comprising: front and rear panels joined together by a crotch panel, said front and rear panels having respective laterally spaced parallel side edges and free outer end edges defining pairs of laterally spaced corners with said side edges, an elongated strap having an inner end fixed to each of said corners and extending outwardly therefrom parallel to said side edges, a waist strap having a central part spaced outwardly from the free outer end edge of said front panel and secured at right angels to both of the front panel straps, said waist strap having elongated end parts extending in opposite directions away from said front panel straps, said front and rear panel straps being of a length that when said harness is in its position of use on a patient carried on a support unit said straps may be secured around anchoring points disposed behind the patient and above at least his waist, and the end parts of said waist strap being of a length for connection around other anchoring points disposed to either side of said patient.

2. The security harness of claim 1 wherein said crotch panel has laterally spaced side edges inwardly recessed to accommodate the legs of a patient.

* * * * *